United States Patent
Aldabe Arregui et al.

(10) Patent No.: US 7,829,077 B2
(45) Date of Patent: Nov. 9, 2010

(54) TREATMENT OF HEPATITIS C WITH COMPOSITIONS COMPRISING ONCOSTATIN M AND INTERFERON ALPHA

(75) Inventors: Rafael Aldabe Arregui, Pamplona (ES); Esther Larrea Leoz, Pamplona (ES); María Pilar Civeira Murillo, Pamplona (ES); Jesús Prieto Valtueña, Pamplona (ES)

(73) Assignee: Proyecto De Biomedicina Cima, S.L., Pamplona (Navarra) (ES)

( * ) Notice: Subject to any disclaimer, the term of this patent is extended or adjusted under 35 U.S.C. 154(b) by 0 days.

(21) Appl. No.: 11/922,221

(22) PCT Filed: Jun. 16, 2006

(86) PCT No.: PCT/ES2006/000353

§ 371 (c)(1), (2), (4) Date: Jul. 21, 2008

(87) PCT Pub. No.: WO2006/134195

PCT Pub. Date: Dec. 21, 2006

(65) Prior Publication Data

US 2009/0130055 A1  May 21, 2009

(30) Foreign Application Priority Data

Jun. 16, 2005 (ES) .................. 200501468

(51) Int. Cl.
- A61K 38/21 (2006.01)
- A61K 45/00 (2006.01)
- A61K 39/00 (2006.01)
- A61K 38/00 (2006.01)
- C07K 14/56 (2006.01)

(52) U.S. Cl. .............. 424/85.7; 424/85.1; 424/198.1; 514/2; 530/351

(58) Field of Classification Search .............. None
See application file for complete search history.

(56) References Cited

U.S. PATENT DOCUMENTS

| | | | |
|---|---|---|---|
| 5,928,636 | A | 7/1999 | Alber et al. |
| 6,177,074 | B1 | 1/2001 | Glue et al. |
| 6,284,237 | B1 | 9/2001 | Clark et al. |
| 6,348,191 | B1 | 2/2002 | Clark et al. |
| 6,461,605 | B1 | 10/2002 | Cutler et al. |
| 6,509,154 | B1 | 1/2003 | de Paillette |
| 6,524,570 | B1 | 2/2003 | Glue et al. |
| 6,685,931 | B1 | 2/2004 | Grint et al. |

FOREIGN PATENT DOCUMENTS

| | | |
|---|---|---|
| EP | 1 001 801 | 5/2000 |
| EP | 0 858 343 | 3/2004 |
| ES | 2 006 776 | 5/1989 |
| ES | 2 224 246 | 3/2005 |
| WO | 00/37096 | 6/2000 |

OTHER PUBLICATIONS

Patterson, B.K., et al. Leukemia inhibitory factor inhibits HIV-1 replication and is upregulated in placentae from nontransmitting women. J. Clin. Invest. 2001, vol. 107, p. 287-294.*

Chevaliez S et al. Interferons and their use in persistent viral infections. Handbook of Experimental Pharmacology. 2009, vol. 189, p. 203-241.*

International Search Report issued Jan. 4, 2007 in the International (PCT) Application of which the present application is the U.S. National Stage.

Hoofnagle et al., "Randomized, Controlled Trial of Recombinant Human α-Interferon in Patients with Chronic Hepatitis B," Gastroenterology, Nov. 1988, vol. 95, pp. 1318-1325.

Manns et al., "Peginterferon alfa-2b Plus Ribavirin Compared with Interferon alfa-2b Plus Ribavirin for Initial Treatment of Chronic Hepatitis C: A Randomised Trial," The Lancet, Sep. 22, 2001, vol. 358, pp. 958-965.

Gale et al., "Evidence That Hepatitis C Virus Resistance to Interferon is Mediated Through Repression of the PKR Protein Kinase by the Nonstructural 5A Protein," Virology (1997), vol. 230, (Article No. VY978493) pp. 217-227.

Taylor et al., "Inhibition of the Interferon-Inducible Protein Kinase PKR by HCV E2 Protein," Science (1999) vol. 285, pp. 107-110.

Blindenbacher et al., "Expression of Hepatitis C Virus Proteins Inhibits Interferon α Signaling in the Liver of Transgenic Mice," Gastroenterology (2003), vol. 124, pp. 1465-1475.

Duong et al., "Hepatitis C Virus Inhibits Interferon Signaling Through Up-Regulation of Protein Phosphatase 2A," Gastroenterology (2004), vol. 126, pp. 263-277.

Heinrich et al., "Interleukin-6-Type Cytokine Signalling Through the gp130/Jak/STAT Pathway," Biochem J. (1998), vol. 334, pp. 297-314.

(Continued)

Primary Examiner—Robert Landsman
Assistant Examiner—Bruce D Hissong
(74) Attorney, Agent, or Firm—Wenderoth, Lind & Ponack, LLP

(57) ABSTRACT

The invention relates to the use of at least one cytokine from the IL-6 family -gp130, preferably selected from among IL-11, the leukaemia inhibitory factor (LIF), oncostatin M (OSM), cardiotrophin-1, ciliary neurotrophic factor (CNTF), the cardiotrophin-like cytokine (CLC) and combinations thereof or a DNA sequence encoding same, in the preparation of a pharmaceutical composition which is intended for combined administration with at least one IFN-α or a DNA sequence encoding same, for use in the treatment of viral diseases. The invention also relates to a pharmaceutical composition comprising a pharmaceutically-acceptable quantity of at least one cytokin from the IL-6 family –gp130 or a DNA sequence encoding same and a pharmaceutically-acceptable quantity of at least one IFN-α or a DNA sequence encoding same, a pharmaceutical kit and a method for the treatment of viral diseases with the combined administration of the aforementioned cytokines and IFN-α.

22 Claims, 5 Drawing Sheets

OTHER PUBLICATIONS

Zhu et al., "STAT3 Induces Anti-Hepatitis C Viral Activity in Liver Cells," Biochemical and Biophysical Research Communications (2004), vol. 324, pp. 518-528.

Pietschmann et al., "Persistent and Transient Replication of Full-Length Hepatitis C Virus Genomes in Cell Culture," Journal of Virology (Apr. 2002), vol. 76, No. 8, pp. 4008-4021.

Chomczynski et al., "Single-Step Method of RNA Isolation by Acid Guanidinium Thiocyanate-Phenol-Chloroform Extraction," Analytical Biochemistry (1987), vol. 162, pp. 156-159.

International Search Report issued Jan. 4, 2007 in the International (PCT) Application of which the present application is the U.S. National Stage.

* cited by examiner

TREATMENT OF HEPATITIS C WITH COMPOSITIONS COMPRISING ONCOSTATIN M AND INTERFERON ALPHA

This application is a U.S. national stage of International Application No. PCT/ES2006/000353 filed Jun. 16, 2006.

The present invention relates to the use of a cytokine in combination with an interferon for the preparation of compositions designed for the treatment of viral diseases.

STATE OF THE ART

The interferon (IFN) system is the first line of defense against viral diseases in mammals. Type I interferons (which include several IFN-α and IFN-β subtypes) are molecules with antiviral activity, which are induced in mammal cells in response to viral infections. The action of IFN-α is mediated by interaction with a surface cellular receptor multi-subunit, which consists of two receptor subunits, IFN-α receptor 1 (IFNAR1) and IFNAR2. Only one IFNAR1 chain form has been identified; and three variants of the IFNAR2 subunit have been recognised: one that is full-length, IFRNAR2c, and two truncated isoforms, IFNAR2b and IFNAR2a. The IFNAR2c variant is involved in binding with ligands and the transduction of signals, whilst the two truncated forms, IFNAR2b and IFNAR2a—which do not have intracellular domains-, inhibit the IFN-α signal, through competition with IFNAR2c for binding with IFN-α.

The IFN-α signalling cascade is initiated when IFN-α binds with the receptor. The binding of IFN-α with the receptor leads to the activation of tyrosine-kinases associated with IFNAR (Janus kinase 1 (Jak1) and tyrosine-kinase 2 (Tyk2)), which phosphorylate both subunits, IFNAR1 and IFNAR2. Phosphorylated IFNAR1 provides a binding-point for the signal transduction and activator of transcription 2 (STAT2), which contains a homology-2 domain with Src, when phosphorylated by Tyk2 or Jak1. The other STATs, including STAT1, STAT3 and STAT5, are consequently recruited to the receptor for phosphorylation and activation. The activated monomers STAT1 and STAT2 are then once again released to the cytosol, where they form heterodimers and bind with the interferon regulatory factor 9/Protein p48, to form an active transcription factor complex known as interferon-stimulated gene factor 3 (ISGF3). The complex is translocated to the nucleus and binds with the IFN stimulation response element (ISRE) in order to initiate the transcription of target genes, including some antiviral and immunoregulatory proteins. IFN-α also induces the formation of other STAT complexes, including STAT1/STAT1, STAT1/STAT3 and STAT3/STAT3, which bind with the activated γ sequence in the promoter regions of sensitive genes. In primary human hepatocytes, IFN-α activates STAT1, STAT2, STAT3 and STAT5, followed by the induction of a wide variety of antiviral and proapoptotic genes which may contribute to IFN-α's anti-tumour and antiviral activity in the human liver.

In contrast with IFN-α, which activates STAT1, STAT2 and STAT3, in the case of type II IFN (IFN γ), binding with the receptor leads to the exclusive phosphorylation of STAT1 by Jak1 and Jak2, and this is followed by the homodimerisation of STAT1 and nuclear translocation of the homodimer.

Viral infections represent a great health problem throughout the world. Among the viruses that cause chronic infections, the viruses which cause hepatitis B (HBV) and hepatitis C (HCV) are important as the main etiological factors of chronic viral hepatitis and hepatic cirrhosis; these disorders affect over 500 million people throughout the world (about 300 million affected by HBV and 200 million by HCV). HBV causes chronic infection primarily in cases of vertical transmission and immunodepressed individuals. On the other hand, HCV infection is noteworthy due to its tendency to develop chronicity in most cases, which suggests that this virus has developed particularly effective mechanisms to avoid the interferon system. Patients suffering from chronic HCV infection, as well as patients suffering from chronic hepatitis B, fail to respond to interferon therapy. In chronic hepatitis B, sustained antiviral response takes place in less than 40% of the cases [1]. In the case of chronic hepatitis C, although the majority of patients infected with genotypes HCV 2 or 3 exhibit a sustained virological response (SVR) after 24 or 28 weeks of combination therapy with pegylated IFN-α and ribavirin [2], only 50% of those infected with genotype 1 achieved SVR with this therapeutic regime [2]. Since over 80% of patients infected with HCV in the Western world and Asia correspond to genotype 1, more efficient means are urgently needed in order to increase IFN-α's antiviral effectiveness. The underlying mechanisms of resistance to IFN-α observed in HCV and other chronic viral diseases are still poorly understood and there is a great need to find therapeutic strategies with which to overcome resistance to IFN-α therapy in these diseases.

The response to interferon-α by the cell infected with the virus is dependent on several determining factors, including those related to the virus and those specific ones related to the host. Various HCV gene products have been shown to modulate the host's response to IFN therapy and affect the severity of the viral disease, particularly in the case of hepatic disease. It has been noted that HCV non-structural (NS5A) and structural (E2) proteins interact with PKR, one of the key molecules involved in the development of an antiviral state in response to IFN [3, 4]. This could block PKR, leading to inhibition of the IFN activity in HCV-infected cells. On the other hand, several studies have shown that the STAT1 signal induced by IFN-α is affected both in transgenic mice with HCV and in liver biopsies of patients with chronic HCV [5, 6].

It has been observed that, in HCV-infected liver samples, and in liver cells carrying a genomic HCV replicon (full-length), there is a marked reduction in the quantity of IFNAR2 and STAT3 mRNA. A relevant finding has been that activation of STAT1, STAT2 and STAT3 by IFN-α was blocked in liver cells containing a full-length HCV replicon, which suggests that HCV replication may block IFN-α signalling in the infected cells. It is also interesting that STAT1 activation in these cells is not affected when they were incubated with the pro-inflammatory molecule IFN-γ, which suggests that the blocking of STAT1 activation produced by HCV is specific for the type 1 IFN signalling cascade, and does not affect the type II IFN signalling pathway.

There are other cytokines which activate the Jak-STAT signalling pathway, particularly members of the IL-6 family, which comprises IL-6, IL-11, leukemia-inhibiting factor (LIF), oncostatin (OSM), cardiotrophin-1 (CT-1), ciliary neurotrophic factor (CNTF) and cardiotrophin-like cytokine (CLC) [7]. These cytokines bind with the plasma membrane's receptor complexes which comprise the common gp130 transduction signal receptor chain [7]. The transduction of signals entails the activation of the members of the Jak tyrosine-kinase family, leading to the activation of transcription factors STAT1 and STAT3. These cytokines potentially activate STAT3 and, to a lesser extent, STAT1 through a common gp130 receptor subunit. However, although it has been shown that IL-6 induces some antiviral effects [8], this cytokine's antiviral activity is much lower than that of interferon-α.

The present invention relates to the use of an IL-6 family interleukin, preferably cardiotrophin-1 (CT-1) or oncostatin M (OSM):

(1) in order to enhance interferon-alpha's (IFN-α) antiviral activity;
(2) in order to overcome the resistance to interferon observed in patients suffering from chronic viral infection, who do not respond to IFN-α therapy (by itself or associated with other antiviral components);
(3) in order to achieve a combined treatment of an IL-6 family interleukin, preferably CT-1 or OSM, plus IFN-α as improved antiviral therapy for any type of viral infection, and particularly infection with the hepatitis C virus (HCV), wherein the preferred combination CT-1-IFN-α or OSM-IFN-α has proven to be especially potent in the inhibition of HCV replication.

The present invention has achieved the following objectives:

(1) showing that the combination of IFN-α with an IL-6 family interleukin, and preferably with CT-1 and OSM, produces a more potent antiviral effect than that induced by a cytokine (IFN or IL-6 family cytokine) alone; and
(2) showing that IFN-α associated with an IL-6 family cytokine, particularly CT-1 or oncostatin M, is able to overcome the blocking of the IFN-α signalling cascade (and, consequently, the attenuation of the IFN-α effect which is produced when the virus, preferably HCV, replicates in the infected cell).

DESCRIPTION OF THE INVENTION

The present invention relates, in the first place, to the use of at least one IL-6 family cytokine -gp130 family—or a DNA sequence which codes for it, in the preparation of a pharmaceutical composition for combined administration with at least one IFN-α or a DNA sequence which codes for it, in the treatment of viral diseases, being said cytokine selected among cardiotrophin-1, IL-11, leukemia-inhibiting factor, oncostatin M, ciliary neurotrophic factor, cardiotrophin-like cytokine, and combinations thereof; and, even more preferably, said cytokine is cardiotrophin-1 or oncostatin M.

As used in the present invention, the "IL-6 family" cytokine, for example, CT-1, relates to:
the complete native form of said cytokine;
any active fraction of said cytokine, that is, any partial polypeptide sequence of said cytokine which maintains the physiological effects of the complete cytokine claimed in the present invention; and
any polypeptide derivative of said cytokine, that is, any polypeptide sequence which has a homology greater than 80% with said native cytokine and maintains the physiological effects of the complete cytokine claimed in the present invention.

The IL-6 family cytokine (whether it is complete, an active fraction or a polypeptide derivative) may come from both the native form and any form of recombinant cytokine, starting from any polynucleotide form which codes for the complete cytokine, the active fraction or the polypeptide derivative.

Moreover, within the protein of the IL-6 family, considered complete or as an active fraction, or within the recombinant cytokine one or several aminoacids could have been deleted, substituted or added to the protein by any of the mentioned ways, provided that its foreseen activity on the present invention is maintained.

On the other hand, according to the present invention, the IFN-α of the invention is any type of IFN-α. In a specific embodiment, said IFN-α is selected from IFN-α-2a, IFN-α-2b, IFN-α-5, consensus interferon, purified IFN-α, pegylated IFN-α and combinations thereof. In another specific embodiment, the IFN-α is selected from pegylated IFN-α-2b, pegylated IFN-α-2a, pegylated IFN-α-5 and combinations thereof.

The combined use of an IFN-α and an IL-6 family cytokine is designed for the treatment of a preferably viral disease. As an example of viral diseases which may be treated through the combined use of interferon and an IL-6 family cytokine, the following can be mentioned, amongst others: diseases caused by the encephalomyocarditis virus, hepatitis B and C, HIV, cutaneous viral infections (chicken-pox, herpes zoster, measles), respiratory viral infections, viral infections of the central nervous system, hepatic viral infections, viral infections of the salivary glands, infectious mononucleosis and genital warts.

Preferably, the viral disease is hepatitis C.

Furthermore, according to the present invention, the IL-6 family cytokine—or cytokines—and the IFN-α may be administered separately, being present in different pharmaceutical compositions; or they may be administered jointly, being present in the same pharmaceutical composition.

An additional object of the present invention is, therefore, a pharmaceutical composition which comprises a pharmaceutically acceptable quantity of at least one IL-6 family cytokine -gp130 family—, or a DNA sequence which codes for it, and a pharmaceutically acceptable quantity of at least one IFN-α, or a DNA sequence which codes for it.

In said pharmaceutical composition, which comprises at least one IFN-α, or a DNA sequence which codes for it, and at least one IL-6 family cytokine, or a DNA sequence which codes for it, the IL-6 family cytokine is preferably selected from IL-6, IL-11, leukemia-inhibiting factor, oncostatin M, cardiotrophin-1, ciliary neurotrophic factor, cardiotrophin-like cytokine and combinations thereof; and even more preferably, said IL-6 family cytokine is cardiotrophin-1 or oncostatin M.

In the pharmaceutical composition of the invention, the IFN-α is any type of IFN-α. In a preferred embodiment, the IFN-α has been selected from IFN-α-2a, IFN-α-2b, IFN-α-5, consensus interferon, purified IFN-α, pegylated IFN-α and combinations thereof. In another additional preferred embodiment, the IFN-α is selected from pegylated IFN-α-2b, pegylated IFN-α-2a, pegylated IFN-α-5 and combinations thereof.

In a specific embodiment, the DNA sequence that codes for the IL-6-family cytokine (whether it is complete, an active fraction or a polypeptide derivative) or the IFN-α is incorporated into an expression vector, for example, a plasmid or viral vector, which is preferably operatively binded with a control sequence that regulates the expression of the cytokine or the IFN-α. The construction of said expression vector with the DNA sequence may be performed by conventional recombinant technology methods contained in handbooks such as, for example, "Molecular Cloning: A Laboratory Manual", by J. Sambrook, D. W. Russel Eds. 2001, 3rd ed. Cold Spring Harbor, N.Y. These embodiments of the pharmaceutical composition are of interest for therapies which use gene transfer (gene therapy).

The pharmaceutical composition of the invention may further comprise at least one excipient that is pharmaceutically compatible with the IL-6-family cytokine, or with the DNA sequence that codes for it, and pharmaceutically compatible with the IFN-α or the DNA sequence that codes for it.

Furthermore, in the pharmaceutical composition, the IL-6-family cytokine—or the DNA sequence that codes for it—and the IFN-α—or the DNA sequence which codes for it—may be carried in respective carrier agents.

Valid examples of the pharmaceutical composition of the invention include, without being limited thereto, any solid composition (for example, tablets, capsules, granules, etc.) or liquid composition (for example, solutions, suspensions, emulsions, etc.) for administration by any appropriate administration route, for example, oral, nasal, parenteral, topical, transdermal, rectal, etc.

In a specific embodiment, said pharmaceutical composition may be in an oral administration pharmaceutical form, either solid or liquid. Illustrative examples of oral administration pharmaceutical forms include tablets, capsules, granulates, solutions, suspensions, etc., and may contain the conventional excipients, such as bonding, diluent, disintegrating, lubricant, wetting, etc., excipients, and may be prepared by conventional methods. The pharmaceutical composition may also be adapted for parenteral administration, in the form of, for example, sterile solutions, suspensions or lyophilised products, in the appropriate dosage form; in this case, said pharmaceutical composition shall include the adequate excipients, such as buffers, surfactant excipients, etc. In any event, the excipients shall be selected on the basis of the selected administration pharmaceutical form. A review of the different pharmaceutical forms for drug administration, for these and other potential alternative routes, and their preparation, may be found, for example, in the book "Tecnología farmacéutica" ["Pharmaceutical Technology"], by J. L. Vila Jato, 1997 Vols. I and II, Ed. Síntesis, Madrid; or in "Handbook of Pharmaceutical Manufacturing Formulations", by S. K. Niazi, 2004 Vols. I to VI, CRC Press, Boca Raton.

In a specific embodiment, the pharmaceutical composition is designed for parenteral administration, preferably subcutaneous, intravenous, intramuscular or intraperitoneal.

In a specific embodiment of the pharmaceutical composition of the invention, the IFN-α is in pegylated form. Some examples for the preparation of compositions with pegylated forms may be found in U.S. Pat. No. 5,762,923 and U.S. Pat. No. 5,766,582. It is also possible to purchase some of these pegylated forms commercially, such as, for example, PEG-Intron (pegylated IFN-α-2b) by Schering Corporation (Kenilworth, N. J., U.S.A.) and PEGASYS (IFN-α-2a) by Hoffmann La Roche (Nutley, N. J., U.S.A.).

For application in therapy, both the IL-6-family cytokine and the IFN-α shall preferably be in a pharmaceutically acceptable or substantially pure form, i.e. they shall have a pharmaceutically acceptable purity level, excluding pharmaceutically acceptable excipients and not including material considered to be toxic at the normal dosage levels. The purity levels for the IL-6 family cytokine and the IFN-α are preferably above 50%, more preferably, above 70% and more preferably, above 90%. In a preferred embodiment, they are above 95%.

In general, the therapeutically effective quantity of the IL-6 family cytokine and the IFN-α to be administered shall be dependent, amongst other factors, on the individual who is to be treated, the severity of the disease suffered by said individual, the selected form of administration, etc. For this reason, the doses mentioned in the present invention shall be considered solely as guides for persons skilled in the art, and the latter shall adjust the doses on the basis of said variables. However, the IL-6 family cytokine and the IFN-α may be administered one or more times a day, for example, 1, 2, 3 or 4 times a day.

As an illustrative example, and without this limiting the scope of protection, in a specific embodiment wherein cardiotrophin-1 and IFN-α-2a (or 2b) are combined, the typical total daily quantity of cardiotrophin-1 shall be between 1 µg/kg and 10 mg/kg of body weight; and the typical total daily quantity of IFN-α-2a is between 1.5 and 10 MIU per day or between 40 and 300 micrograms per week of pegylated IFN-α. Normally, the dosage level will be higher during the first weeks of treatment, with the dose being reduced in subsequent stages. Likewise, the administration scheme may be daily, three times per week, or also weekly. On the other hand, the cardiotrophin-1 and the IFN-α may be administered following different administration schemes (for example, different administration route or different frequency).

An additional objective of the present invention is a pharmaceutical kit for the treatment of a viral disease which includes at least:
  a first component which comprises at least one IL-6 family cytokine -gp130 family—(either complete, an active fraction or a polypeptide derivative, as they have been defined above) or a DNA sequence that codes for said cytokine; and
  a second component which comprises at least one IFN-α or a DNA sequence that codes for said IFN-α.

The kit according to the invention preferably comprises an IL-6 family cytokine selected from IL-6, IL-11, leukemia-inhibiting factor, oncostatin M, cardiotrophin-1, ciliary neurotrophic factor, cardiotrophin-like cytokine and combinations thereof, and, even more preferably, the IL-6 family cytokine is cardiotrophin-1 or oncostatin M.

The kit according to the invention comprises an IFN-α of any type, preferably one selected from IFN-α-2a, IFN-α-2b, IFN-α-5, consensus interferon, purified IFN-α, pegylated IFN-α and combinations thereof. In another additional preferred embodiment, the IFN-α is selected from pegylated IFN-α-2b, pegylated IFN-α-2a, pegylated IFN-α-5 and combinations thereof.

In a specific embodiment, the DNA sequence which codes for the IL-6 family cytokine (whether complete, an active fraction or a polypeptide derivative) or the IFN-a in the kit is incorporated into an expression vector.

In the kit of the present invention, the first component and the second component may comprise, in addition, at least one pharmaceutically acceptable excipient which is compatible with the IL-6 family cytokine—or a DNA sequence that codes for it—and with the IFN-α or a DNA sequence that codes for it—.

According to the present invention, the kit defined above may comprise the first and the second components in separate pharmaceutical compositions; or else the first and the second components may be present in the kit in the same pharmaceutical composition.

This kit may also comprise a third component, which comprises one or more excipients that are pharmaceutically compatible with the IL-6 family cytokine—or a DNA sequence that codes for it—and with the IFN-α—or a DNA sequence that codes for it—.

Said third component may comprise, in addition, one or more carrier agents which are pharmaceutically compatible with the IL-6 family cytokine—or a DNA sequence that codes for it—and with the IFN-α—or a DNA sequence that codes for it—.

An additional object of the present invention is a method for the treatment of a viral disease which comprises administering in a combined manner a therapeutically effective quantity of at least one IL-6 family —gp130 family—cytokine (whether complete, an active fraction or a polypeptide derivative, as they have been previously defined), or a DNA sequence that codes for it, and a therapeutically effective quantity of at least one IFN-α, or a DNA sequence that codes for it.

In a specific embodiment, the DNA sequence that codes for the IL-6 family cytokine or the IFN-α of the method is incorporated into an expression vector.

In the method defined above, the viral disease may be produced by the encephalomyocarditis virus, hepatitis B and C, HIV, cutaneous viral infections (chicken-pox, herpes zoster, measles), respiratory viral infections, viral infections of the central nervous system, hepatic viral infections, viral infections of the salivary glands, infectious mononucleosis and genital warts.

According to a preferred embodiment of the method of the invention, the viral disease is hepatitis C.

According to the method of the invention, the IL-6 family cytokine is preferably selected from IL-6, IL-11, leukemia-inhibiting factor, oncostatin M, cardiotrophin-1, ciliary neurotrophic factor, cardiotrophin-like cytokine and combinations thereof; even more preferably, the IL-6 family cytokine is cardiotrophin-1 or oncostatin M.

In the method defined according to the invention, the IFN-α is any type of IFN-α. In a preferred embodiment, it is selected from IFN-α-2a, IFN-α-2b, IFN-α-5, consensus interferon, purified IFN-α, pegylated IFN-α and combinations thereof; in another additional preferred embodiment, the IFN-α is selected from pegylated IFN-α-2b, pegylated IFN-α-2a, pegylated IFN-α-5 and combinations thereof.

Furthermore, according to the method of the invention, the latter may comprise the combined and simultaneous administration of the interleukin family cytokine, preferably cardiotrophin-1, and the IFN-α.

In this method, the IL-6 family cytokine (whether complete, an active fraction or a polypeptide derivative) and the IFN-α may be present in the same pharmaceutical composition which is administered to the patient; or else the IL-6 family cytokine and the IFN-α may be administered in separate pharmaceutical compositions.

The present invention shows that, when the hepatic cells which comprise a complete HCV replicon are stimulated with IFN-α and an IL-6 family interleukin, particularly cardiotrophin-1 or oncostatin M:

(1) the inhibiting effect of HCV on STAT3 phosphorylation, which takes place when the cells are incubated with IFN-α alone or with an IL-6 family cytokine (for example, CT-1 or OSM) alone, is overcome.

(2) there is a higher induction of interferon-sensitive genes (ISGs), such as 2'-5'-oligoadenylate synthase (2'-5' OAS), and higher levels of STAT1 and STAT3 than when the cells are incubated with cytokine alone; and (3) replication of the virus is more effectively inhibited than when cytokine is used alone.

(4) Interaction between IFN-α and CT-1, or between IFN-α and OSM, is of strong sinergism.

EMBODIMENTS OF THE INVENTION

Experiment 1

Figure 1:
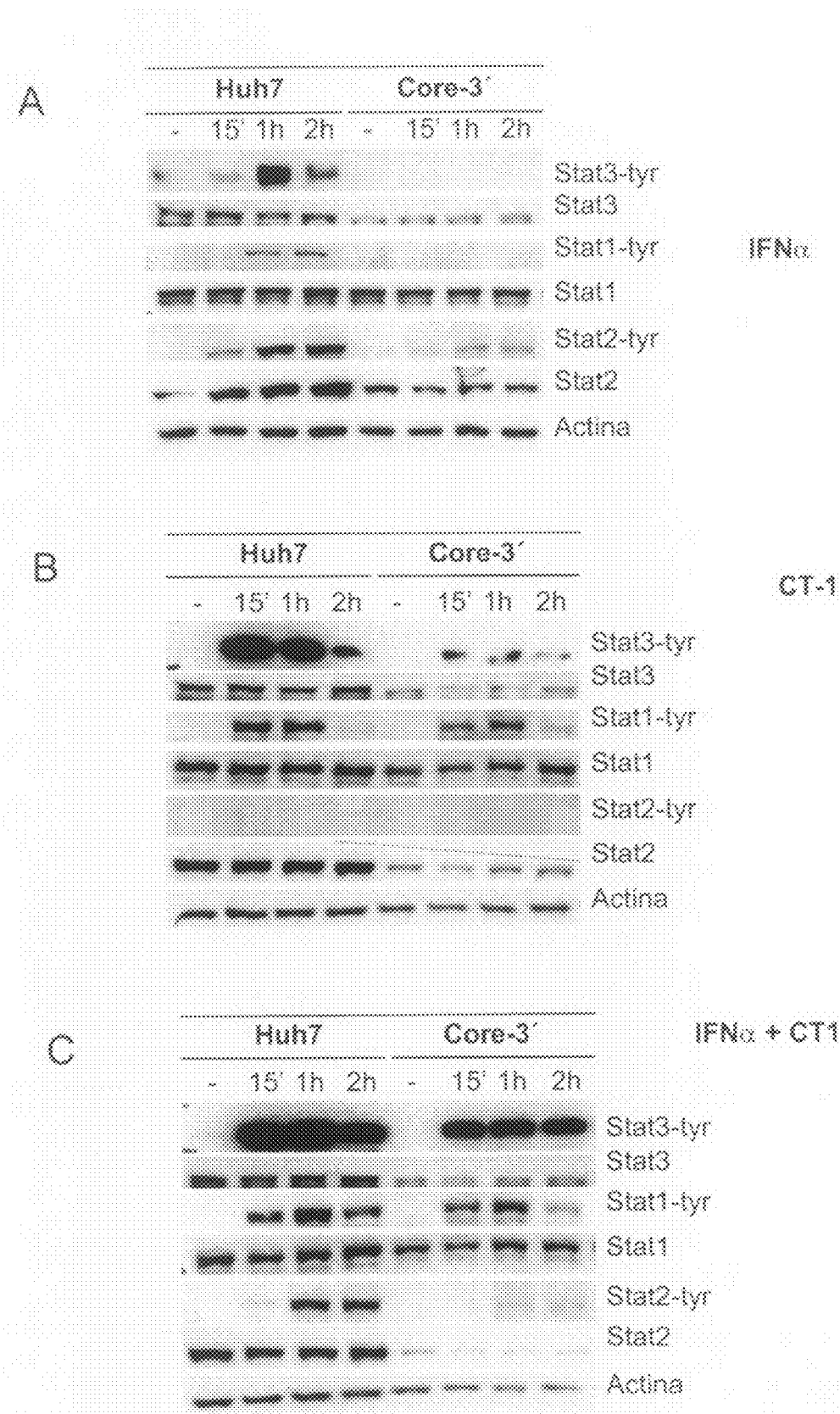
FIG. 1 shows an analysis of the phosphorylation of STAT1, STAT2 and STAT3. Huh7 cells (Huh7) and Huh7 cells containing a complete genomic HCV replicon (Core-3') were treated for 15, 60 and 120 minutes with 50 IU/ml of IFN-α-2 (IFN-α) or with 20 ng/ml of cardiotrophin-1 (CT-1), or with a combination of IFN-α-2 and CT-1, and the quantities of phosphorylated STAT1, STAT2 and STAT3 present in the cellular extracts were analysed by means of Western blot.

Study of the Effect of the Combination of IFN-α-2 and CT-1 on the Signalling Cascade in Cells that Maintain HCV Replication (FIG. 1)

In non-transfected Huh7 cells (a hepatoma cell line), the addition of 50 IU/ml of IFN-α-2 (IFN-α-2) induced the phosphorylation of STAT1, STAT2 and STAT3, with maximum activation of STAT1 and STAT2 at 1 hour and 2 hours, and of STAT3 at 1 hour (see FIG. 1A). However, in Huh7 cells transfected with a full-length HCV replicon, a marked inhibition of STAT1, STAT2 and STAT3 phosphorylation was observed after incubation with IFN-α-2. Therefore, there was a complete absence of activated STAT3 and STAT1 and a marked inhibition of STAT2 activation (see FIG. 1A).

On the other hand, in non-transfected Huh7 cells, it was found that the addition of 20 ng/ml of CT-1 led to the activation of both STAT3 and STAT1 (more intensely in the case of STAT3), with maximum values at 15 minutes and 1 hour, and a substantial decrease at 2 hours (FIG. 1B). As expected, CT-1 did not induce any STAT2 activation. In Huh7 cells transfected with a complete HCV replicon, the activation of STAT3 by CT-1 was substantially reduced, whilst the phosphorylation of STAT1 was only slightly affected (FIG. 1B).

When non-transfected Huh7 cells were incubated with a mixture of 50 IU/ml of IFN-α-2 and 20 ng/ml of CT-1, a more intense and lasting phosphorylation of STAT3 and STAT1 was detected than when the cells were incubated with each of the cytokines alone. The activation of STAT2 was similar to that found with IFN-α-2 alone. It is significant that, when the Huh7 cells transfected with a complete HCV replicon were incubated with the IFN-α-2 (50 IU/ml) plus CT-1 (20 ng/ml) mixture, STAT3 phosphorylation took place without any damage, with the activation of STAT3 being not only more intense, but also more lasting than when the non-transfected cells were incubated with IFN-α-2 alone (FIG. 1C). This fact is noteworthy, because, as has been mentioned (and is shown in FIGS. 1A and 1B), HCV replication in Huh7 cells seriously reduces the activation of STAT3 by both IFN-α-2 and by CT-1 separately, and it is therefore surprising that this blockage disappears by incubating the cells with the two cytokines together; this opens a new prospect for a promising strategy in the treatment of viral diseases. It must also be noted that, when IFN-α-2 and CT-1 are combined to treat cells with HCV replication, not only is a potent, sustained activation of STAT3 produced, but also an activation of STAT1 similar to that found when non-transfected cells are incubated with CT-1 alone and more intense than when non-transfected cells are incubated with IFN-α-2 alone (compare FIGS. 1A and 1B). It is important to note that IFN-α-2 was unable to activate STAT1 in cells with sustained HCV replication, whilst the combination of CT-1 plus IFN-α-2 was able to very effectively activate this important antiviral factor in cells with HCV replication. This clearly shows that combining IFN-α-2 and CT-1 leads to an improvement in antiviral activity, allowing for STAT2 phosphorylation, albeit at levels that are clearly lower than when cells without HCV replication are used (see FIG. 1C).

In conclusion, when the cells with sustained HCV replication were treated with IFN-α-2 in an isolated fashion, there was no STAT1 and STAT3 activation, and only low levels of STAT2 were observed. The absence of activated STAT1 and STAT3—two important inducers of the cell's antiviral state— could prevent the formation of the STAT1-STAT2 heterodimers, the STAT1-STAT3 heterodimers, and the STAT1 and STAT3 homodimers, thus collapsing the cell's antiviral defense. The use of CT-1 in combination with IFN-α-2 allows for the formation of high levels of activated STAT1 and STAT3, thus restoring the cell's viral resistance mechanism.

In the experiments shown in FIG. 1, one can see that the HCV infection not only leads to a defective activation of STAT1, but also to a reduction in the STAT3 and STAT2 protein levels. The studies represented in FIG. 1 show the short-term effects of incubation with either IFN-α-2 or CT-1, or with a combination of both. The experiments described below show that, with incubation for 72 hours, one can observe that the combined treatment with CT-1 and IFN-α-2, or OSM and IFN-α-2, led to an increased expression of STAT3, thus counteracting the effect of HCV in the infected cells (see FIG. 2).

Experimental Method 1

Establishment of Huh 7 cell lines carrying the full-length HCV replicon. Huh7 cells were established which expressed the full-length HCV replicon as has been described [9]. In sum, pI$_{389}$/Core-3'/5.1 were linearised with ScaI (New England Biolabs, USA) and were used as templates for RNA synthesis using T7 RNA polymerase (Promega, USA). 20 μg of synthesised RNA were used to electrophore $10^7$ Huh7 cells and, 24 hours later, 500 μg/ml of G418 (Gibco, USA) were added. Twice a week, the supplemented culture medium was replaced by G418 and, 4 weeks after transfection, the mixed colonies resistant to G418 were collected and used for subsequent analysis.

Western-blot analysis. Huh7 cells which either expressed the full-length HCV replicon or not were seeded at 200,000/well in 6-well plates in D-MEM (Gibco) with 10% FCS (Gibco). 50 IU/ml of IFN-α-2 (Intron A, Schering-Plough), or 20 ng/ml of CT-1 (R&D Systems, UK), or a combination of IFN-α-2 (50 IU/ml) plus CT-1 (20 ng/ml) were added for different periods of time: 15 minutes, 1 hour and 2 hours. Subsequently, the Huh7 cells were lysed in lysis buffer (60 mM Tris-HCl pH 6.8, 2% SDS, 2.5% glycerol, 0.7 M 2-mercaptoethanol and 0.02% bromophenol blue). The samples were resolved in SDS-polyacrylamide gels (Bio-Rad Laboratories, CA) at 7.5% under reducing conditions. Following electrophoresis, they were transferred to nitrocellulose membranes (Bio-Rad Laboratories) and dyed with Ponceau red solution (Sigma-Aldrich, Germany), in order to verify that there was an equal load of proteins. The membranes were incubated in TBS-T (50 mM Tris-HCl (pH 7.6), 200 mM NaCl and 0.1% Tween-20) with 5% dehydrated milk. The proteins were detected by incubation with the specific primary antibody in TBS-T for 1 hour. The membranes were subsequently washed in TBS-T and secondary antibody conjugated with peroxidase was added for 1 hour. The membranes were subject to extensive washing in TBS-T and the specific protein bands were viewed using the "Western Lightning Chemiluminescence Reagent Plus" chemiluminescence detection system (Perkin Elmer, USA), following the manufacturer's instructions. Subsequently, the membranes were autoradiographed and the bands were quantified by means of densitometric analysis performed by means of the Molecular Analyst/PC programme (Bio-Rad Laboratories).

Antibodies. The anti-phospho-STAT1$^{tyr701}$ and anti-phospho-STAT3$^{tyr705}$ antibodies and the anti-rabbit IgG antibody conjugated to HRP were purchased from Cell Signaling Technology (USA). The anti-STAT3, anti-phospho-STAT1$^{ser727}$, anti-STAT2 and anti-phospho-STAT2$^{tyr689}$ antibodies were obtained from Upstate Biotechnology (USA). The anti-STAT1 antibody was from Santa Cruz Biotechnology (Santa Cruz, Calif.). The anti-actin antibody was from Sigma-Aldrich (Germany).

In order to determine whether the combination of an IL-6 family cytokine with IFN-α leads to a stronger antiviral state in the cell, we performed additional experiments designed to: a) evaluate whether the combination therapy of IFN-α plus the IL-6 family cytokine can increase the expression of interferon-sensitive genes more intensely than any of the cytokines by itself; b) determine whether the combination therapy of IFN-α plus the IL-6 family cytokine could be more potent in inhibiting HCV replication than each cytokine separately; c) evaluate whether the combination therapy of IFN-α-2 plus CT-1 could be more efficient in defending the cells against the cytopathic effects of a non-HCV-related virus, and; d) determination of the kind of interaction between IFN-α and the IL-6 family cytokine.

Figure 2:
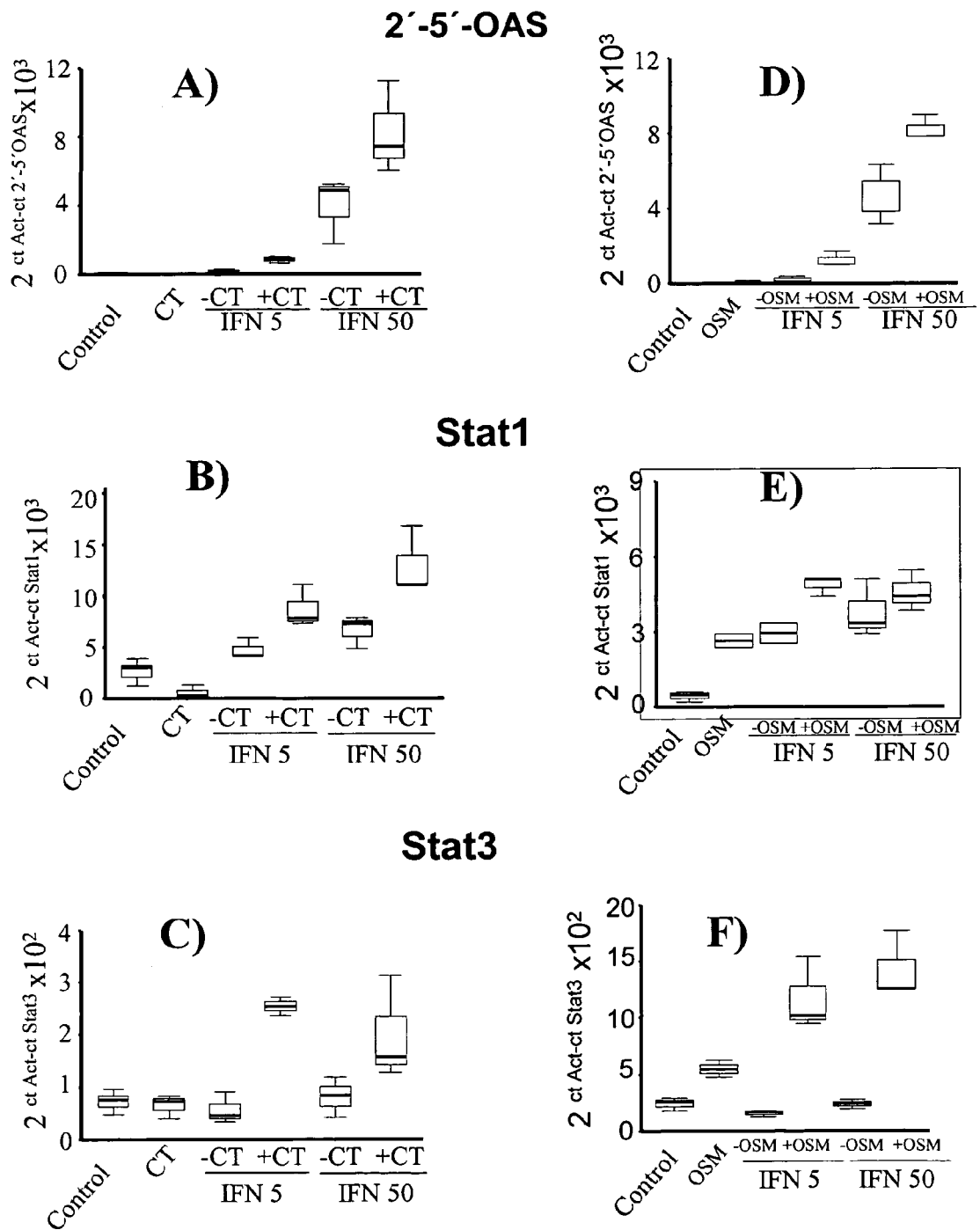
FIG. 2 shows a quantitative real-time RT-PCR analysis of the STAT1, STAT3 and 2'-5' OAS mRNA present in Huh7 cells containing a complete HCV replicon, treated for 3 days with 5 or 50 IU/ml of IFN-α-2 (IFN 5, IFN 50), alone (−CT) or in combination with 20 ng/ml of CT-1 (+CT); and with 5 or 50 IU/ml of IFN-α-2, alone (−OSM) or in combination with 20 ng/ml of OSM (+OSM). Control: untreated cells.

Experiment 2. Evaluation of the effect of the combination therapy of IFN-α-2 plus CT-1, or IFN-α-2 plus OSM, on the induction of interferon-sensitive-genes (ISGs) (FIG. 2)

The expression of the ISGs 2'-5' OAS, STAT1 and STAT3 was studied on Huh7 cells carrying the HCV replicon after incubation for 72 hours with IFN-α-2 (5 or 50 IU/ml) or CT-1 (20 ng/ml), or OSM (20 ng/ml), or IFN-α-2+OSM combined (see FIGS. 2A-2F). We observe that, whilst CT-1 or OSM by itself were not able to increase or weakly the expression of these ISGs, the addition of CT-1 or OSM to low or high doses of IFN-α-2 led to a marked increase in the expression of the ISGs, which indicates that CT-1 or OSM can significantly enhance the capacity of IFN-α-2 to increasingly regulate antiviral genes in cells supporting viral replication. Although the three ISGs analysed herein have significant antiviral effects, the increase in the expression of STAT3 by combining CT-1 or OSM and IFN-α-2 is particularly relevant, since this factor does not only have antiviral properties, but also exhibits a potent cytoprotection and anti-inflammatory activity.

Experimental Method 2

Real-time RT-PCR analysis of the expression of the ISGs' mRNA. Huh7 cells expressing the full-length HCV replicon were seeded at 100,000/well in 6-well plates in D-MEM (Gibco), with 10% FCS (Gibco). 50 or 5 IU/ml of IFN-α-2 by itself or in combination with 20 ng/ml of CT-1, or with 20 ng/ml OSM, were added. The cell culture was maintained for three days. The supplemented culture medium was replaced daily with said cytokines. The total RNA was obtained following the "Ultraspec RNA Isolation System" protocol (Biotech, USA), which is based on the method described by Chomczynski and Sacchi [10]. Two micrograms of total RNA were treated with DNAase (Gibco-BRL, UK) prior to reverse transcription with M-MLV Reverse Transcriptase (Gibco BRL) in the presence of RNaseOUT (Gibco-BRL). The expression of the STATs, the 2-5OAS and the β-actin was measured by means of real-time PCR using an Icycler and the IQ SYBR Green Supermix (Bio-Rad Laboratories, CA). 2-μl aliquots of the cDNA pool were used for each PCR, which contained specific forward and reverse direction primers for each gene (Table 1) in a final volume of 20 μl. In order to determine the specificity of the obtained PCR products, their dissociation temperature was analysed. The results were normalised on the basis of the quantification of β-actin in the same sample. The quantity of each transcript was expressed through the formula $2^{ct(actin)-ct(gene)}$, with ct being the point at which the fluorescence significantly increases above the background fluorescence.

TABLE 1

Primers used in this study

| Gene | Forward direction primer (5'-3') | Reverse direction primer (5'-3') |
| --- | --- | --- |
| 2'-5'OAS | SEQ. ID. NO: 1 TTAAGAGGCAACTCCGATGG | SEQ. ID. NO: 2 AGCAGACTGCAAACTCACCA |
| STAT1 | SEQ. ID. NO: 3 GCTATTCACAACCACTCATTCA | SEQ. ID. NO: 4 ACAAGATACAGCCACATAGACA |
| STAT3α | SEQ. ID. NO: 5 GTCCGTGGAACCATACACAA | SEQ. ID. NO: 6 CAATGGTATTGCTGCAGGTG |
| β-actin | SEQ. ID. NO: 7 AGCCTCGCCTTTGCCGA | SEQ. ID. NO: 8 CTGGTGCCTGGGGCG |
| HCV | SEQ. ID. NO: 9 CCTGTGAGGAACTACTGTCT | SEQ. ID. NO: 10 CTATCAGGCAGTACCACAAG |

Figure 3:
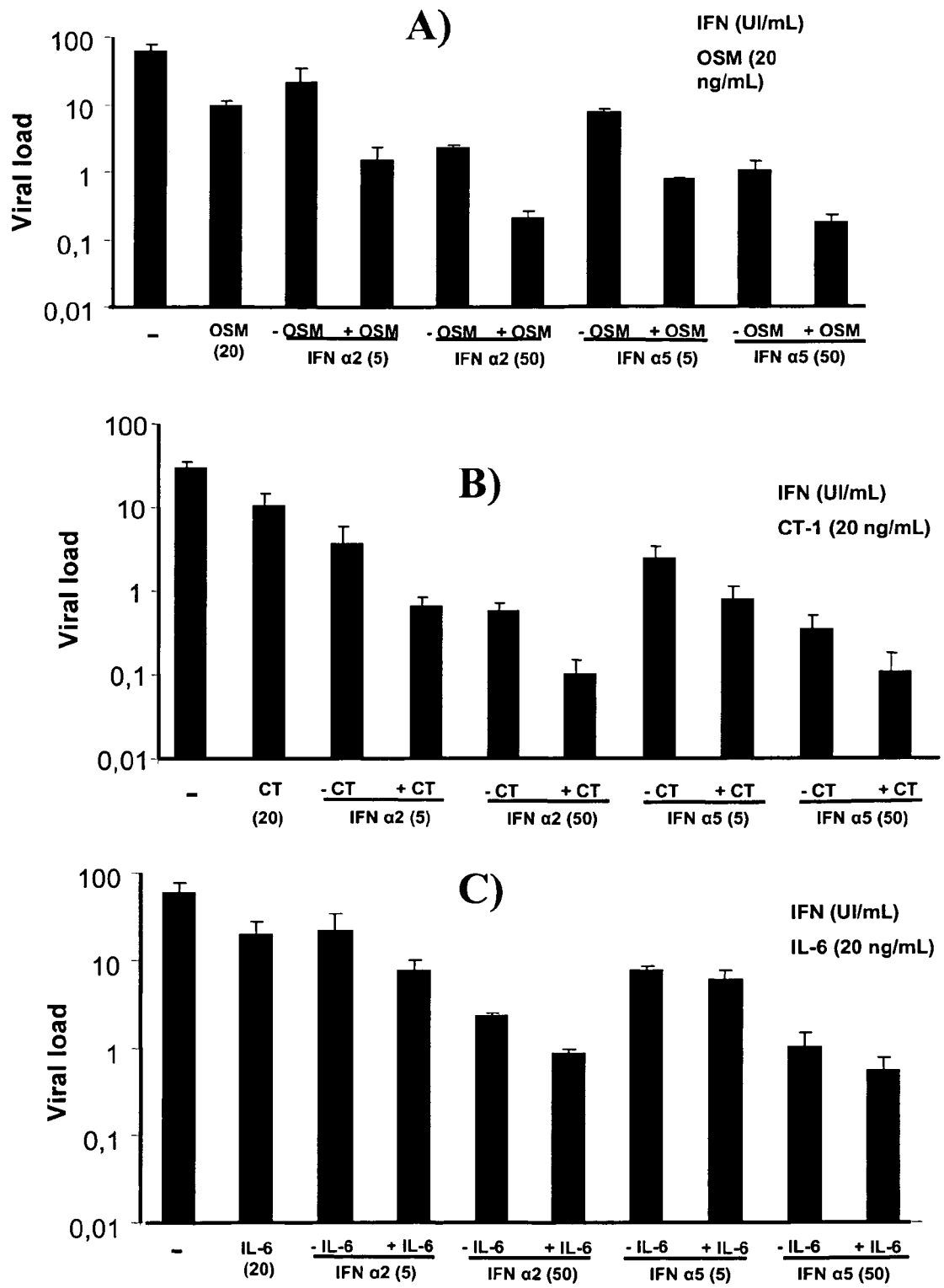
FIG. 3 shows a quantitative real-time RT-PCR analysis of the HCV RNA present in Huh7 cells containing a complete HCV replicon, treated for 3 days with 5 or 50 IU/ml of IFN-α-2 or IFN-α-5, and 20 ng/ml of CT-1 or OSM or IL-6.

Experiment 3. Study of the effects of the combination of IFN-α-2 plus an IL-6 family cytokine on HCV replication in Huh 7 cells transfected with the full-length HCV replicon (FIG. 3)

Due to the stronger induction of ISGs observed upon combining IFN-α-2 plus CT-1 or OSM, it was desired to analyse whether this combination was superior to IFN-α-2 by itself, or to the IL-6 family cytokine by itself, in the reduction of the viral load in cells with the full-length HCV replicon. Thus, Huh7 cells carrying the HCV replicon were incubated with IFN-α (IFN-α-2 or IFN-α-5, at 5 or 50 IU/ml) plus or minus the IL-6 family cytokine (IL-6, CT-1, OSM; at 20 ng/ml); or with the IL-6 family cytokines by themselves. The quantity of HCV RNA was measured after 72 hours of culture (FIGS. 3$^a$, 3B, 3C). In FIG. 3, one can see that the IL-6 family cytokines: IL-6, CT-1 and OSM by themselves have a modest antiviral effect. However, CT-1 and OSM strongly enhanced the antiviral effect both of IFN-α-2 as of IFN-α-5 when these cytokines were used at low (5 IU/ml) or high (50 IU/ml) doses (FIGS. 3A and 3B). IL-6 enhanced in a weaker way the antiviral effect, both of IFN-α-2 as of IFN-α-5 (FIG. 3C). Thus, the combination therapy of IFN-α-2 or IFN-α-5 plus CT-1 or OSM increases the antiviral effect of IFN-α by an approx. factor of 5 and 10 respectively. Further, the combination therapy of IFN-α-2 or IFN-α-5 plus IL-6 enhances it in an approx. factor of 2.

Figure 4:
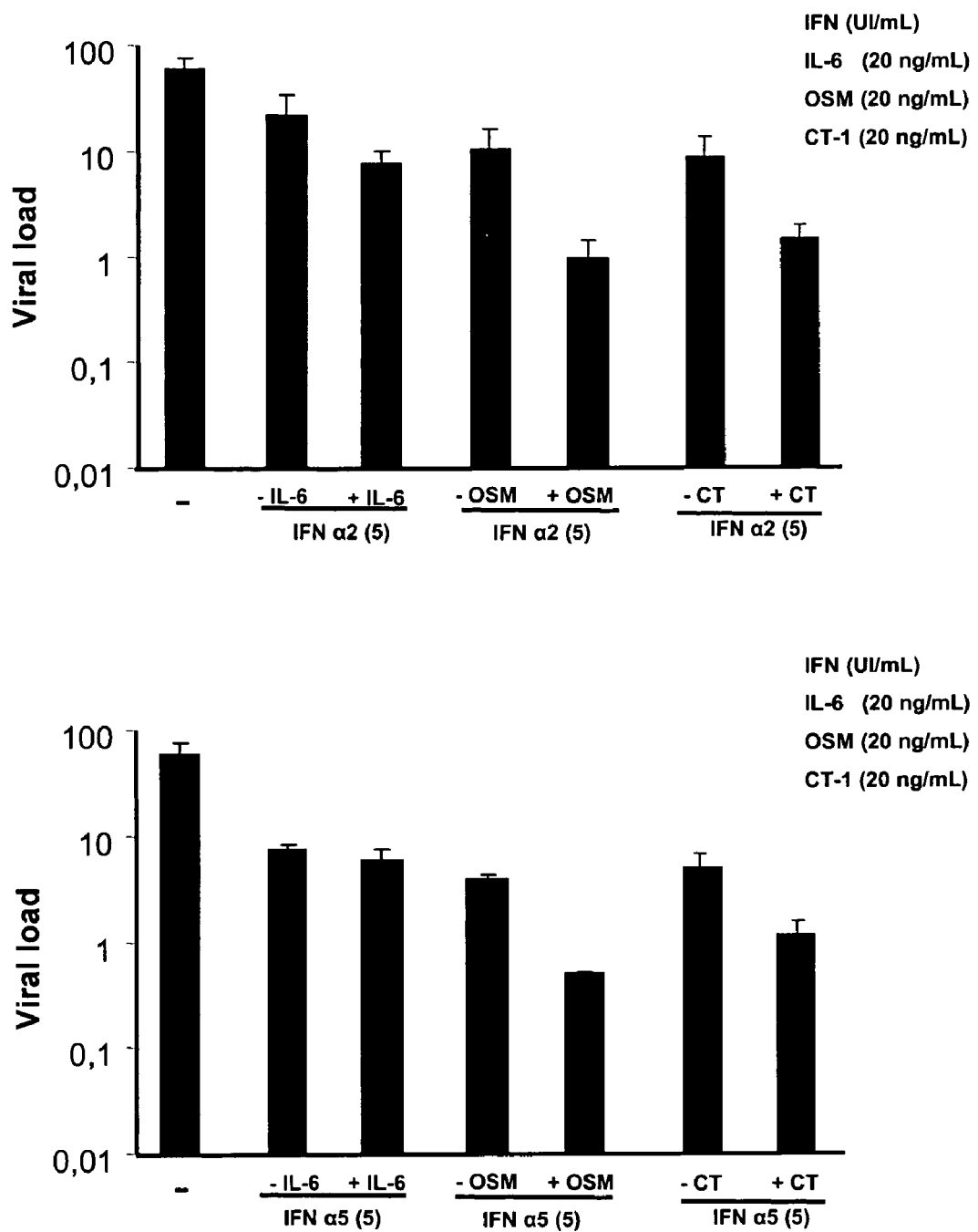
FIG. 4 shows the antiviral comparative effect of the combination IFN-α-2 or IFN-α-5 (5 U/ml) plus CT-1 or OSM or IL-6 (20 ng/mL), by RT-PCR in real time, of the HCV RNA present in Huh7 cells containing a complete HCV replicon treated for 3 days with said cytokines.

In FIG. 4 it is comparatively represented the enhanced effect of the IL-6, the CT-1 and the OSM (20 ng/mL) on the antiviral action of the IFN-α-2 (5 U/mL) (FIG. 4A) or of the IFN-α-5 (FIG. 4B). The higher enhancer antiviral effect of the combinations IFN-α/CT-1 and IFN-α/OSM against the combination IFN-α/IL-6 is clearly observed.

Experimental method 3

Quantitative real-time PCR analysis of HCV RNA. Huh7 cells expressing the full-length HCV replicon were seeded at 100,000/well in 6-well plates in D-MEM with 10% FCS. 50 or 5 IU/ml of IFN-α-2 or IFN-α-5 by themselves, or in combination with 20 ng/ml of CT-1 or OSM or IL-6 were added. The cell culture was maintained for three days. The supplemented culture medium was replaced daily with said cytokines.

The total RNA of Huh7 cells transfected with the full-length HCV replicon was obtained following the "Ultraspec RNA Isolation System" protocol (Biotech, USA), which is based on the method described by Chomczynski and Sacchi [10]. Two micrograms of total RNA were treated with DNAase (Gibco-BRL) prior to reverse transcription with M-MLV Reverse Transcriptase (Gibco BRL) in the presence of RNaseOUT (Gibco-BRL). The expression of the HCV RNA and the P-actin mRNA was measured by quantitative real-time PCR using an Icycler and the IQ SYBR Green Supermix (Bio-Rad Laboratiories). 2-μl aliquots of the cDNA pool were used for each PCR, which contained specific forward and reverse direction primers for the 5 non-translated region of the HCV or the β-actin gene (Table 1) in a final volume of 20 μl. In order to determine the specificity of the PCR products, their dissociation temperature was analysed. The results were normalised on the basis of the quantification of β-actin in the same sample. The quantity of HCV RNA was expressed through the formula $2^{ct(actin)-ct(HCV)}$, with ct being the point at which the fluorescence significantly increases above the background fluorescence.

Figure 5:
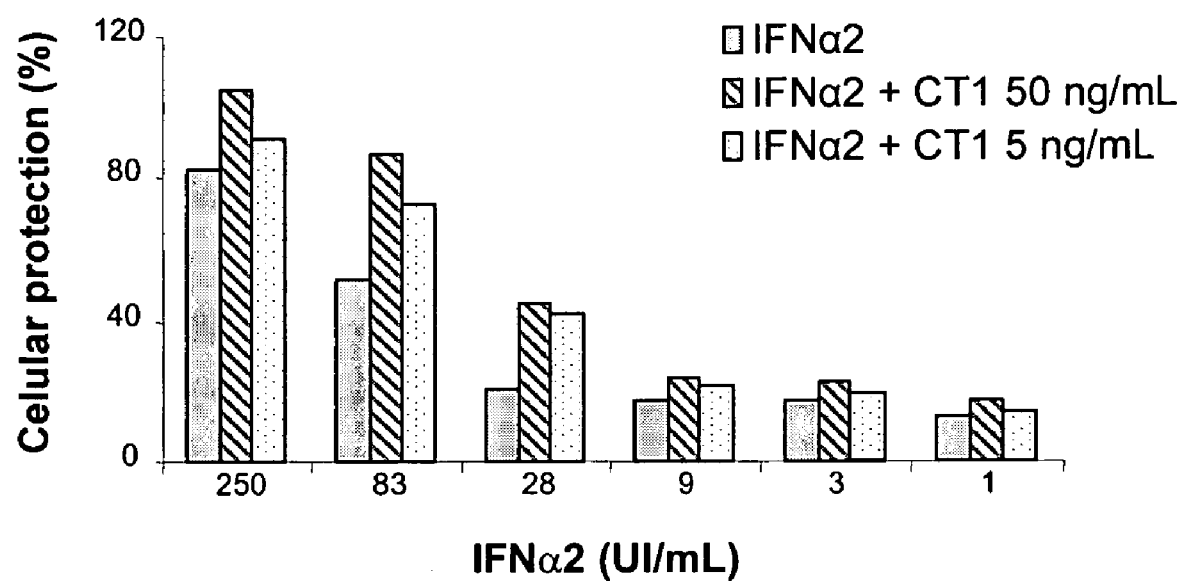
FIG. 5 shows the percentage of Huh7 cells protected against infection by the encephalomyocarditis virus. Huh7 cells were pre-treated for 24 hours with 5 ng/ml or 50 ng/ml of CT-1 and different quantities of IFN-α-2, and were infected with $10^5$ PFU of the encephalomyocarditis virus (EMCV), and, after 24 hours, the cells were dyed with crystal violet stain in order to measure the quantity of viable cells.

Experiment 4. Study of the effects of the combination of IFN-α-2 plus CT-1 in the defense against the cytopathic effects of the encephalomyocarditis Virus (EMCV) (FIG. 5).

In order to determine whether the synergic effect of combination therapy is also produced in other viral infections different from HCV, we analysed the protection obtained with this treatment against the cytopathic effect of EMCV in Huh7 cells. Huh7 cells were incubated with decreasing doses of IFN-α-2, from 250 to 1 IU/ml, in the presence or absence of a low (5 ng/ml) or high (50 ng/ml) dose of CT-1 and were infected with EMCV 24 hours later. We observe that CT-1 by itself (at a low or high dose) had little cytoprotection effect on the EMCV-infected cells, since the addition of this cytokine at very low doses of IFN-α-2 did not improve cell viability. However, CT-1, at both low and high doses, markedly increased the protection induced by IFN-α-2 against the cytopathic effect of EMCV. This synergy was observed upon using IFN-α-2 doses between 250 and 28 IU/ml, with the synergy being most pronounced at IFN-α-2 doses of 83 and 28 IU/ml. These data show that the antiviral synergy of IFN-α-2 and CT-1 is not limited to HCV, but is applied to a broad range of viral diseases.

Experimental Method 4.

Cytoprotection assay of IFN-α-2 and CT-1 against EMCV in Huh7 cells. The cytoprotection activity of IFN-α-2 and CT-1 was determined by measuring these cytokines' capacity to protect Huh7 cells against the cytopathic effect of the encephalomyocarditis virus. The assay was performed on a 96-well microtitre plate. Firstly, $2\times10^4$ Huh7 cells per well were seeded in 150 μl of a medium containing serial dilutions of IFN-α-2 by itself (from 250 to 1 IU/ml) or these serial dilutions of IFN-α-2 plus 50 or 5 ng/ml of CT-1, and they were incubated for 24 hours. $10^5$ PFU of EMC virus were added per well and the cytopathic effect at 24 hours was measured as follows: after eliminating the medium, the wells were washed twice with PBS and dyed with crystal violet colouring solution (0.5% in methanol-water 1:4 v/v). The optical density at 540 nm was read. The results are expressed as the percentage of cells protected against the cytopathic effect of EMCV.

Experiment 5. Study of the effects between IFN-α and various interleukin 6 family cytokines on HCV replication in Huh 7 cells transfected with the full-length HCV replicon Due to the enhancer antiviral effect shown by the combination of IFN-α and an IL-6 family cytokine, it was desired to determine the kind of interaction set up in the combination of IFN-α-2 or IFN-α-5 with the IL-6 family cytokines: IL-6, OSM and CT-1.

Several antiviral tests were performed combining fixed concentrations of IFN-α-2 and IFN-α-5 (5 or 50 IU/ml) with or without IL-6, OSM and CT-1 (20 ng/mL) in Huh7 cells transfected with the full-length HCV replicon. Mathematical analysis on the kind of interaction set up between IFN-α and the IL-6 family cytokines was performed by multi-variant analysis according to the method described by T. C. Chou (11). The kind of interaction between two substances is measured by a factor named Interaction Index "I", where I=d1/D1+d2/D2; being d1, d2, the inhibitors rates on the combination, and D1, D2, the rate of each inhibitor that would effect the same effect as the combination. Then, "I" equal to 1 means that both substances do not react between them (additive effect); "I" lower than 1 means that the combination is synergic; and a value of "I" larger than 1 means that the combination is antagonist. Table 2 shows standard synergic rates in respect to the value of "I".

TABLE 2

| INTERACTION INDEX (I) | KIND OF SYNERGISM |
|---|---|
| 0.1-0.3 | STRONG SYNERGISM |
| 0.3-0.7 | SYNERGISM |
| 0.7-0.85 | MODERATE SYNERGISM |
| 0.85-0.89 | LIGHT SYNERGISM |
| 0.90-1.10 | ADDITIVE EFFECT |

Interaction indexes obtained for the different combination of IFN-α and the previously described IL-6 family cytokines were in all cases lower than 1, thus the combination of IFN-α (2 or 5) and such cytokines IL-6, OSM and CT-1 being synergic (Table 3). Furthermore, the obtained data show that the synergic effect is always remarkable higher at combinations IFN-α/OSM and IFN-α/CT-1 (I<0.3 strong synergism) that at the combination IFN-α/IL-6 (I<0.7 synergism)

TABLE 3

| CYTOKINE COMBINATION | INTERACTION INDEX (I) |
|---|---|
| IFN-α-2 (5 U/mL) + OSM (20 ng/mL) | 0.29 |
| IFN-α-2 (50 U/mL) + OSM (20 ng/mL) | 0.11 |
| IFN-α-5 (5 U/mL) + OSM (20 ng/mL) | 0.26 |
| IFN-α-5 (50 U/mL) + OSM (20 ng/mL) | 0.17 |
| IFN-α-2 (5 U/mL) + CT-1 (20 ng/mL) | 0.22 |
| IFN-α-2 (50 U/mL) + CT-1 (20 ng/mL) | 0.25 |
| IFN-α-5 (5 U/mL) + CT-1 (20 ng/mL) | 0.25 |
| IFN-α-5 (50 U/mL) + CT-1 (20 ng/mL) | 0.13 |
| IFN-α-2 (5 U/mL) + IL-6 (20 ng/mL) | 0.44 |
| IFN-α-2 (50 U/mL) + IL-6 (20 ng/mL) | 0.45 |
| IFN-α-5 (5 U/mL) + IL-6 (20 ng/mL) | 0.40 |
| IFN-α-5 (50 U/mL) + IL-6 (20 ng/mL) | 0.29 |

Experimental Method 5

Quantitative real-time PCR analysis of the HCV RNA. Huh7 cells expressing the full-length HCV replicon were seeded at 20,000/well in 24-well plates in D-MEM with 10% FCS. Different experiments were performed; 50 or 5 IU/ml of IFN-α-2 or IFN-α-5 with or without 20 ng/ml of CT-1, OSM or IL-6 (R&D Systems, UK) were added. The cell culture was maintained for three days. The supplemented culture medium was replaced with said cytokines daily.

The total RNA of Huh7 cells transfected with the full-length HCV replicon was obtained using the Kit Nucleic Acid Purification Lysis Solution (Applied BioSystems, Foster City, Calif.) and the semi-automatic system ABI PRISM 6100 Nucleic Acid PrepStation (Applied BioSystems). Two micrograms of total RNA were treated with DNAase (Gibco-BRL) prior to reverse transcription with M-MLV Reverse Transcriptase (Gibco BRL) in the presence of RNaseOUT (Gibco-BRL). The expression of the HCV RNA and the β-actin mRNA was measured by quantitative real-time PCR using an Icycler and the IQ SYBR Green Supermix (Bio-Rad Laboratiories). 2-μl aliquots of the cDNA pool were used for each PCR, which contained specific forward and reverse direction primers for the 5 non-translated region of the HCV or the β-actin gene (Table 1) in a final volume of 20 μl. In order to determine the specificity of the PCR products, their dissociation temperature was analysed. The results were normalised on the basis of the quantification of γ-actin in the same sample. The quantity of HCV RNA was expressed through the formula $2^{ct(actin)-ct(HCV)}$, being ct the point at which the fluorescence significantly increases above the background fluorescence.

For the calculation of the Interaction Index the following equation was applicable:

$$I = d1/D1 + d2/D2$$

REFERENCES

1. Hoofangle J H, Peters M, Mullen K D, Jones D B, Rustgi V, Di Bisceglie A, Hallahan C, Park Y, Meschievitz C, Jones E A. Randomized, Controlled Trial of Recombinant Human Alpha-Interferon in Patients with Chronic Hepatitis B. Gastroenterlogy 1988; 95:1318-1325.
2. Manns M P, McHutchison J G, Gordon S C, Rustgi V K, Shiffman M, Reindollar R, Goodman Z D, Koury K, Ling M, Albrecth J K. Peginterferon Alfa-2b plus Ribavirin Compared with Interferon Alfa-2b plus Ribavirin for Initial Treatment of Chronic Hepatitis C: A Randomized Trial. Lancet 2001; 358:958-965.
3. Gale M J, Jr., Korth M J, Tang N M, Tan S L, Hopkins D A, Dever T E, Polyak S J, Gretch D R, Katze M G. Evidence that Hepatitis C Virus Resistance to Interferon Is Mediated through Repression of the PKR Protein Kinase by the Nonstructural 5A Protein. Virology 1997; 230:217-227.
4. Taylor D R, Shi S T, Romano P R, Barber G N, Lai M M. Inhibition of the Interferon-Inducible Protein Kinase PKR by HCV E2 Protein. Science 1999; 285:107-110.
5. Blindenbacher A, Duong F H, Hunziker L, Stutvoet S T, Wang X, Terracciano L, Moradpour D, Blum H E, Alonzi T, Tripodi M, La Monica N, Heim M H. Expression of Hepatitis C Virus Protein Inhibits Interferon Alpha Signalling in the Liver of Transgenic Mice. Gastroenterology 2003; 124:1465-1475.
6. Duong F H, Filipowicz M, Tripodi M, La Monica N, Heim M H. Hepatitis C Virus Inhibits Interferon Signaling through Up-Regulation of Protein Phosphatase 2A. Gastroenterology 2004; 126:263-277.

7. Heinrich P C, Behrmann I, Muller-Newen G, Schaper F, Graeve L. IL-6-Type Cytokine Signalling through the gp130/Jak/STAT Pathway. Biochem J 1998; 334:297-314.
8. Zhu H, Shang X, Terada N, Liu C. STAT3 Induces Anti-Hepatitis C Viral Activity in Liver Cells. Biochem Biophys Res Commun 2004; 324:518-528.
9. Pietschmann T, Lohmann V, Kaul A, Krieger N, Rinck G, Rutter G, Strand D, Bartenschlager R. Persistent and Transient Replication of Full-Length Hepatitis C Virus Genomes in Cell Culture. J Virol 2002; 76:4008-4021.
10. Chomczynski P, Sacchi N. Single-Step Method of RNA Isolation by Acid Guanidium Thiocyanate-Phenol-Chloroform Extraction. Anal Biochem 1987; 162:156-159.
11. Chou TC. Synergism and Antagonism in chemotherapy 1991; 61-102. Academic Press.

The invention claimed is:

1. A pharmaceutical composition for the treatment of a viral disease caused by hepatitis C virus comprising a pharmaceutically acceptable quantity of oncostatin M, and a pharmaceutically acceptable quantity of at least one interferon (IFN)-α.

2. The pharmaceutical composition according to claim 1, wherein oncostain M is the complete native cytokine.

3. The pharmaceutical composition according to claim 1, wherein the IFN-α is selected from the group consisting of: IFN-α-2a, IFN-α-2b, IFN-α-5, consensus Interferon, purified IFN-α, pegylated IFN-α and combinations thereof.

4. The pharmaceutical composition according to claim 1, wherein the IFN-α is selected from the group consisting of: pegylated IFN-α-2b, pegylated IFN-α-2a, pegylated IFN-α-5 and combinations thereof.

5. The pharmaceutical composition according to claim 1, additionally containing at least one excipient which is pharmaceutically compatible with oncostatin M and with IFN-α.

6. The pharmaceutical composition according to claim 1, wherein oncostain M and the IFN-α are carried in respective carrier agents within a same composition.

7. A pharmaceutical kit for the treatment of a viral disease caused by hepatitis C virus, comprising at least:
a first component which comprises oncostatin M,
a second component which comprises at least one IFN-α,
wherein the first and second components are present in the same pharmaceutical composition.

8. The kit according to claim 7, wherein oncostatin M is the complete native cytokine.

9. The kit according to claim 7, wherein the IFN-α is selected from the group consisting of: IFN-α-2a, IFN-α-2b, IFN-α-5, consensus interferon, purified IFN-α, pegylated IFN-α and combinations thereof.

10. The kit according to claim 7, wherein the IFN-α has been selected from the group consisting of: pegylated IFN-α-2b, pegylated IFN-α-2a, pegylated IFN-α-5 and combinations thereof.

11. The kit according to claim 7, additionally comprising a third component, which comprises one or more excipients that are pharmaceutically compatible with oncostatin M, and with the IFN-α.

12. The kit according to claim 7, additionally comprising a third component, which comprises one or more carrier agents that are pharmaceutically compatible with oncostatin M and with the IFN-α.

13. The kit according to claim 7, wherein the first component additionally comprises, at least one excipient, which is pharmaceutically acceptable and compatible with oncostatin M and with the IFN-α.

14. The kit according to claim 7, wherein the second component additionally comprises, one or more excipients which are pharmaceutically acceptable and compatible with oncostatin M and with the IFN-α.

15. A method for the treatment of a viral disease caused by hepatitis C virus, which comprises the combined administration of a therapeutically-effective quantity of oncostatin M, and a therapeutically-effective quantity of at least one IFN-α.

16. The method according to claim 15, wherein the viral disease is hepatitis C.

17. The method according to claim 15, wherein oncostatin M is the complete native cytokine.

18. The method according to claim 15, which comprises the combined and simultaneous administration of oncostatin M and IFN-α.

19. The method according to claim 15, wherein the IFN-α has been selected from the group consisting of: IFN-α-2a, IFN-α-2b, IFN-α-5, consensus Interferon, purified IFN-α, pegylated IFN-α and combinations thereof.

20. The method according to claim 15, wherein the IFN-α is selected from pegylated IFN-α-2b, pegylated IFN-α-2a, pegylated IFN-α-5 and combinations thereof.

21. The method according to claim 15, wherein the oncostatin M and the IFN-α are present in the same pharmaceutical composition that is administered to the patient.

22. The method according to claim 15, wherein oncostatin M and the IFN-α are administered in separate pharmaceutical compositions.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: Synthetic Construct; Synthetic Oligonucleotide

<400> SEQUENCE: 1
ttaagaggca actccgatgg                                                   20

<210> SEQ ID NO 2
<211> LENGTH: 20
<212> TYPE: DNA
<213> ORGANISM: Artificial
<220> FEATURE:
<223> OTHER INFORMATION: Synthetic Construct; Synthetic Oligonucleotide

<400> SEQUENCE: 2
agcagactgc aaactcacca                                                   20

<210> SEQ ID NO 3
<211> LENGTH: 22
<212> TYPE: DNA
<213> ORGANISM: Artificial
<220> FEATURE:
<223> OTHER INFORMATION: Synthetic Construct; Synthetic Oligonucleotide

<400> SEQUENCE: 3
gctattcaca accactcatt ca                                                22

<210> SEQ ID NO 4
<211> LENGTH: 22
<212> TYPE: DNA
<213> ORGANISM: Artificial
<220> FEATURE:
<223> OTHER INFORMATION: Synthetic Construct; Synthetic Oligonucleotide

<400> SEQUENCE: 4
acaagataca gccacataga ca                                                22

<210> SEQ ID NO 5
<211> LENGTH: 20
<212> TYPE: DNA
<213> ORGANISM: Artificial
<220> FEATURE:
<223> OTHER INFORMATION: Synthetic Construct; Synthetic Oligonucleotide

<400> SEQUENCE: 5
gtccgtggaa ccatacacaa                                                   20

<210> SEQ ID NO 6
<211> LENGTH: 20
<212> TYPE: DNA
```

-continued

```
<213> ORGANISM: Artificial
<220> FEATURE:
<223> OTHER INFORMATION: Synthetic Construct; Synthetic Oligonucleotide

<400> SEQUENCE: 6
caatggtatt gctgcaggtg                                                    20

<210> SEQ ID NO 7
<211> LENGTH: 17
<212> TYPE: DNA
<213> ORGANISM: Artificial
<220> FEATURE:
<223> OTHER INFORMATION: Synthetic Construct; Synthetic Oligonucleotide

<400> SEQUENCE: 7
agcctcgcct ttgccga                                                       17

<210> SEQ ID NO 8
<211> LENGTH: 15
<212> TYPE: DNA
<213> ORGANISM: Artificial
<220> FEATURE:
<223> OTHER INFORMATION: Synthetic Construct; Synthetic Oligonucleotide

<400> SEQUENCE: 8
ctggtgcctg gggcg                                                         15

<210> SEQ ID NO 9
<211> LENGTH: 20
<212> TYPE: DNA
<213> ORGANISM: Artificial
<220> FEATURE:
<223> OTHER INFORMATION: Synthetic Construct; Synthetic Oligonucleotide

<400> SEQUENCE: 9
cctgtgagga actactgtct                                                    20

<210> SEQ ID NO 10
<211> LENGTH: 20
<212> TYPE: DNA
<213> ORGANISM: Artificial
<220> FEATURE:
<223> OTHER INFORMATION: Synthetic Construct; Synthetic Oligonucleotide

<400> SEQUENCE: 10
ctatcaggca gtaccacaag                                                    20
```